(12) United States Patent
Zhong et al.

(10) Patent No.: US 6,967,075 B2
(45) Date of Patent: Nov. 22, 2005

(54) HCV REPLICASE COMPLEXES

(75) Inventors: Weidong Zhong, Laguna Naguel, CA (US); Zhi Hong, Aliso Viejo, CA (US); Eric Ferrari, Union, NJ (US)

(73) Assignee: Schering Corporation, Kenilworth, NJ (US)

( * ) Notice: Subject to any disclaimer, the term of this patent is extended or adjusted under 35 U.S.C. 154(b) by 889 days.

(21) Appl. No.: 09/828,034

(22) Filed: Apr. 6, 2001

(65) Prior Publication Data

US 2002/0064771 A1 May 30, 2002

Related U.S. Application Data

(60) Provisional application No. 60/195,852, filed on Apr. 7, 2000.

(51) Int. Cl.[7] .................................................. C12Q 1/70
(52) U.S. Cl. ........................................ 435/5; 435/235.1
(58) Field of Search .................................. 435/5, 235.1

(56) References Cited

PUBLICATIONS

Ago et al., Structure 7: 1417–1426 (1999).
Al et al., Virus Res. 53: 141–149 (1998).
Arnold and Cameron, J. Biol. Chem. 274: 2706–2716 (1999).
Arnold and Cameron, J. Biol. Chem. 275: 5329–5336 (2000).
Bressanelli et al., Proc. Natl. Acad. Sci USA 96:13034–13039 (1999).
Behrens et al., EMBO J. 15: 12–22 (1996).
Carpousis and Gralla, Biochemistry 19: 3245–3253 (1980).
Cheetham & Steitz, Science 286: 2305–2309 (1999).
De Francesco et al., Methods Enzymol. 275: 58–67 (1996).
Ferrari et al., J. Virol. 73: 1649–54 (1999).
Joyce and Steitz, Annu. Rev. Biochem. 63: 777–822 (1997).
Kao et al., Virology 253: 1–7 (1999).
Kuo et al., Science 244: 362–364 (1989).
Lai et al., J. Virol. 73: 10129–10136 (1999).
Lesburg et al., Nat. Struct. Biol. 6: 937–943 (1999).
Lohmann et al., J. Virol. 71: 8416–8428 (1997).
Lohmann et al., Virol. 249: 108–118 (1998).
Love et al., Cell 87: 331–342 (1996).
Luo et al., J. Virol. 74: 851–863 (2000).
Oh et al., J. Virol. 73: 7694–7702 (1999).
Paul et al., Nature 393:280–284 (1998).
Plotch et al., J. Virol. 63: 216–225 (1989).
Yuan et al., Biochem. Biophys. Res. Commun. 232: 231–235 (1997).
Zhong et al., J. Virol. 72:9365–9369 (1998).
Zhong et al., J. Virol. 74: 2017–2022 (2000).

*Primary Examiner*—Laurie Scheiner
(74) *Attorney, Agent, or Firm*—Karen E. Brown

(57) ABSTRACT

This invention provides efficient HCV replicase complexes comprising novel RNA template and primer pair. Assay systems are also provided, which use such complexes, for detecting replicase activity, quantitatively studying the kinetics and mechanism of HCV NS5B-catalyzed nucleotide incorporation, and identifying inhibitors of HCV replicase. The assay systems use small and well-defined synthetic RNAs which allow efficient assembly of all catalytic components in the quaternary complex for HCV NS5B-directed RNA replication. Specific template-primer requirements for efficient RNA synthesis by HCV NS5B replicase are provided for use in assay systems.

19 Claims, No Drawings

SEQUENCE LISTING

<160> NUMBER OF SEQ ID NOS: 33

<210> SEQ ID NO 1
<211> LENGTH: 40
<212> TYPE: RNA
<213> ORGANISM: Artificial Sequence
<220> FEATURE:
<223> OTHER INFORMATION: Description of Artificial Sequence: Synthetic RNA

<400> SEQUENCE: 1
aaaaaaaaaa aaaaaaaaaa aaaaaaaagg acuucggucc                          40

<210> SEQ ID NO 2
<211> LENGTH: 36
<212> TYPE: RNA
<213> ORGANISM: Artificial Sequence
<220> FEATURE:
<223> OTHER INFORMATION: Description of Artificial Sequence: Synthetic RNA

<400> SEQUENCE: 2
ggaaaaaaaa aaaaaaaaaa aaaaaaaaaa aaaaaa                              36

<210> SEQ ID NO 3
<211> LENGTH: 36
<212> TYPE: RNA
<213> ORGANISM: Artificial Sequence
<220> FEATURE:
<223> OTHER INFORMATION: Description of Artificial Sequence: Synthetic RNA

<400> SEQUENCE: 3
ggaaaaaaaa aaaaaaaaaa aaaaaaaaaa aaaaau                              36

<210> SEQ ID NO 4
<211> LENGTH: 36
<212> TYPE: RNA
<213> ORGANISM: Artificial Sequence
<220> FEATURE:
<223> OTHER INFORMATION: Description of Artificial Sequence: Synthetic RNA

<400> SEQUENCE: 4
ggaaaaaaaa aaaaaaaaaa aaaaaaauau auauau                              36

<210> SEQ ID NO 5
<211> LENGTH: 36
<212> TYPE: RNA
<213> ORGANISM: Artificial Sequence
<220> FEATURE:
<223> OTHER INFORMATION: Description of Artificial Sequence: Synthetic RNA

<400> SEQUENCE: 5
ggaaaaaaaa aaaaaaaaaa aaaaaacgcg cgcgcg                              36

<210> SEQ ID NO 6
<211> LENGTH: 10
<212> TYPE: RNA
<213> ORGANISM: Artificial Sequence
<220> FEATURE:
<223> OTHER INFORMATION: Description of Artificial Sequence: Synthetic RNA

<400> SEQUENCE: 6
gcaugggccc                                                           10

-continued

<210> SEQ ID NO 7
<211> LENGTH: 30
<212> TYPE: RNA
<213> ORGANISM: Artificial Sequence
<220> FEATURE:
<223> OTHER INFORMATION: Description of Artificial Sequence: Synthetic RNA

<400> SEQUENCE: 7 gccccccgccc ccgcccccgc ccccgccccc                                              30

<210> SEQ ID NO 8
<211> LENGTH: 4
<212> TYPE: RNA
<213> ORGANISM: Artificial Sequence
<220> FEATURE:
<223> OTHER INFORMATION: Description of Artificial Sequence: Synthetic RNA

<400> SEQUENCE: 8 gucc                                                                            4

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic RNA

<400> SEQUENCE: 9
uccuccuccu ccuccuccuc c                                                        21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic RNA

<400> SEQUENCE: 10
gccgccgccg ccgccgccgc c                                                        21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic RNA

<400> SEQUENCE: 11
accaccacca ccaccaccac c                                                        21

<210> SEQ ID NO 12
<211> LENGTH: 24
<212> TYPE: RNA
<213> ORGANISM: Artificial Sequence
<220> FEATURE:
<223> OTHER INFORMATION: Description of Artificial Sequence: Synthetic RNA

<400> SEQUENCE: 12
gcccgcccgc ccgcccgccc gccc                                                     24

<210> SEQ ID NO 13
<211> LENGTH: 25
<212> TYPE: RNA
<213> ORGANISM: Artificial Sequence
<220> FEATURE:
<223> OTHER INFORMATION: Description of Artificial Sequence: Synthetic RNA -continued

```
<400> SEQUENCE: 13
gccccgcccc gccccgcccc gcccc                                              25

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic RNA

<400> SEQUENCE: 14
aaaaaaaaaa aaaaacaguc c                                                  21

<210> SEQ ID NO 15
<211> LENGTH: 18
<212> TYPE: RNA
<213> ORGANISM: Artificial Sequence
<220> FEATURE:
<223> OTHER INFORMATION: Description of Artificial Sequence: Synthetic RNA

<400> SEQUENCE: 15
aaaaaaaaaa aacagucc                                                      18

<210> SEQ ID NO 16
<211> LENGTH: 15
<212> TYPE: RNA
<213> ORGANISM: Artificial Sequence
<220> FEATURE:
<223> OTHER INFORMATION: Description of Artificial Sequence: Synthetic RNA

<400> SEQUENCE: 16
aaaaaaaaac agucc                                                         15

<210> SEQ ID NO 17
<211> LENGTH: 12
<212> TYPE: RNA
<213> ORGANISM: Artificial Sequence
<220> FEATURE:
<223> OTHER INFORMATION: Description of Artificial Sequence: Synthetic RNA

<400> SEQUENCE: 17
aaaaaacagu cc                                                            12

<210> SEQ ID NO 18
<211> LENGTH: 9
<212> TYPE: RNA
<213> ORGANISM: Artificial Sequence
<220> FEATURE:
<223> OTHER INFORMATION: Description of Artificial Sequence: Synthetic RNA

<400> SEQUENCE: 18 aaacagucc                                                                 9

<210> SEQ ID NO 19
<211> LENGTH: 7
<212> TYPE: RNA
<213> ORGANISM: Artificial Sequence
<220> FEATURE:
<223> OTHER INFORMATION: Description of Artificial Sequence: Synthetic RNA

<400> SEQUENCE: 19 acagucc                                                                   7
```

```
<210> SEQ ID NO 20
<211> LENGTH: 5
<212> TYPE: RNA
<213> ORGANISM: Artificial Sequence
<220> FEATURE:
<223> OTHER INFORMATION: Description of Artificial Sequence: Synthetic RNA

<400> SEQUENCE: 20 agucc                                                                   5

<210> SEQ ID NO 21
<211> LENGTH: 12
<212> TYPE: RNA
<213> ORGANISM: Artificial Sequence
<220> FEATURE:
<223> OTHER INFORMATION: Description of Artificial Sequence: Synthetic RNA

<400> SEQUENCE: 21
aaaaaacagu gc                                                          12

<210> SEQ ID NO 22
<211> LENGTH: 12
<212> TYPE: RNA
<213> ORGANISM: Artificial Sequence
<220> FEATURE:
<223> OTHER INFORMATION: Description of Artificial Sequence: Synthetic RNA

<400> SEQUENCE: 22
aaaaaacagu cg                                                          12

<210> SEQ ID NO 23
<211> LENGTH: 12
<212> TYPE: RNA
<213> ORGANISM: Artificial Sequence
<220> FEATURE:
<223> OTHER INFORMATION: Description of Artificial Sequence: Synthetic RNA

<400> SEQUENCE: 23
aaaaaacagu gg                                                          12

<210> SEQ ID NO 24
<211> LENGTH: 12
<212> TYPE: RNA
<213> ORGANISM: Artificial Sequence
<220> FEATURE:
<223> OTHER INFORMATION: Description of Artificial Sequence: Synthetic RNA

<400> SEQUENCE: 24
aaaaaacagu ac                                                          12

<210> SEQ ID NO 25
<211> LENGTH: 12
<212> TYPE: RNA
<213> ORGANISM: Artificial Sequence
<220> FEATURE:
<223> OTHER INFORMATION: Description of Artificial Sequence: Synthetic RNA

<400> SEQUENCE: 25
aaaaaacagu ca                                                          12

<210> SEQ ID NO 26
<211> LENGTH: 14
<212> TYPE: RNA
<213> ORGANISM: Artificial Sequence
<220> FEATURE:
<223> OTHER INFORMATION: Description of Artificial Sequence: Synthetic RNA
```

```
<400> SEQUENCE: 26
ucugcagauc augu                                                    14

<210> SEQ ID NO 27
<211> LENGTH: 14
<212> TYPE: RNA
<213> ORGANISM: Artificial Sequence
<220> FEATURE:
<223> OTHER INFORMATION: Description of Artificial Sequence: Synthetic RNA

<400> SEQUENCE: 27 aucaggggc uggc                                                     14

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic RNA

<400> SEQUENCE: 28
uccuccuccu ccuccuccaa a                                            21

<210> SEQ ID NO 29
<211> LENGTH: 6
<212> TYPE: RNA
<213> ORGANISM: Artificial Sequence
<220> FEATURE:
<223> OTHER INFORMATION: Description of Artificial Sequence: Synthetic RNA

<400> SEQUENCE: 29 cagucc                                                              6

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic RNA

<400> SEQUENCE: 30
ccaccaccac caccaccacc a                                            21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic RNA

<400> SEQUENCE: 31
caccaccacc accaccacca c                                            21

<210> SEQ ID NO 32
<211> LENGTH: 4
<212> TYPE: RNA
<213> ORGANISM: Artificial Sequence
<220> FEATURE:
<223> OTHER INFORMATION: Description of Artificial Sequence: Synthetic RNA

<400> SEQUENCE: 32 gggg                                                                4
```

```
<210> SEQ ID NO 33
<211> LENGTH: 5
<212> TYPE: RNA
<213> ORGANISM: Artificial Sequence
<220> FEATURE:
<223> OTHER INFORMATION: Description of Artificial Sequence: Synthetic RNA

<400> SEQUENCE: 33 ggggg                                                                   5
```

HCV REPLICASE COMPLEXES

This application claims priority from U.S. Provisional Application No. 60/195,852 filed Apr. 7, 2000 under 35 U.S.C. § 119 (e), which is incorporated herein by reference in its entirety.

FIELD OF THE INVENTION

The present invention relates to HCV replicase complexes comprising novel RNA template and primer pairs, and assay systems comprising the same, for detecting replicase activity and identifying inhibitors of HCV replicase.

BACKGROUND OF THE INVENTION

Infection by hepatitis C virus (HCV) is a compelling human medical problem. HCV is the causative agent for most cases of non-A and non-B hepatitis, with an estimated prevalence of 170 million cases (about 2–3%) globally. Four million individuals may be infected in the United States.

Upon first exposure to HCV, about 10% of infected individuals develop acute clinical hepatitis. In most instances the virus establishes a chronic infection that persists for decades. This usually results in recurrent and progressively worsening liver inflammation, which can lead to a more severe disease state such as cirrhosis and hepatocellular carcinoma.

HCV is an enveloped positive-stranded RNA virus belonging to the Flaviviridae family, and has a genome that encodes a polyprotein of 3010 to 3033 amino acids. The HCV nonstructural (NS) proteins provide the catalytic machinery for viral replication, and are derived by proteolytic cleavage of the polyprotein. A vital enzyme encoded by HCV is NS5B replicase protein, which has RNA-dependent RNA polymerase (RdRp) function and is believed to be responsible for HCV genome replication.

Currently, there are no broadly effective treatments for the debilitating progression of chronic HCV. An understanding of the differences between HCV replicase and cellular polymerases will play an essential role in elucidating the molecular basis of HCV polymerase action to facilitate the design of specific inhibitors against HCV replication. The unique structural features of HCV NS5B replicase [see, e.g., Bressanelli et al., Proc. Natl. Acad. Sci USA 96:13034–13039 (1999); Ago et al., Structure 7: 1417–1426 (1999); Lesburg et al., Nat. Struct. Biol. 6: 937–943 (1999)], in combination with detailed kinetic information about its mechanism of action will help to design specific inhibitors against this polymerase without also targeting cellular polymerases.

The conventional replicase assays used to detect HCV NS5B activity are based on incorporation of radioactive nucleotide substrate into a nascent RNA product. These assays use larger and less defined viral RNA or artificial homopolymeric RNA templates to measure the cumulative incorporation of nucleotides and the average steady state catalytic activity of the polymerase [Behrens et al., EMBO J. 15: 12–22 (1996); De Francesco et al., Methods Enzymol. 275: 58–67 (1996); Ferrari et al., J. Virol. 73: 1649–1654 (1999); Lohmann et al., J. Virol. 71: 8416–8428 (1997)]. Mechanistic data for HCV NS5B-catalyzed nucleotide incorporation is lacking due to the lack of suitable RNA template and primer pairs. Thus, the mechanism of a polymerization reaction or a single turnover event (single nucleotidyl transfer reaction) by HCV replicase is yet unknown, because the conventional template and primer pairs do not assemble efficiently with the replicase enzyme to permit efficient nucleotide incorporation and extension of end-labeled primers.

The conventional assays are also unable to reveal the proportion of enzyme and RNA substrate that is involved in productive binding to form replicase complexes competent for catalysis. The relatively low replicase activity exhibited by these in vitro assays implies that a very small portion of the HCV replicase and RNA template assemble complexes that are competent for catalysis. The conventional assay systems are clearly not suitable for defining the kinetic and thermodynamic constants of HCV NS5B-catalyzed nucleotide incorporation, nor can they be used for mechanistic characterization of inhibitors that target the HCV polymerase protein.

Thus, there is a need in the art for an improved, more accurate assay system for detecting HCV replicase activity. An RNA template-primer pair that allows HCV NS5B to efficiently catalyze nucleotide extension of a labeled primer in a template-dependent fashion will be beneficial. To address this need, the present invention provides an assay system that uses small and well-defined synthetic RNAs which allow efficient assembly of all catalytic components in the quaternary complex for HCV NS5B-directed RNA replication.

SUMMARY OF THE INVENTION

This invention provides specific template-primer requirements for efficient RNA synthesis by HCV NS5B replicase. Templates of the invention are at least five nucleotides long and primers are small (di- or tri-nucleotides are most efficient for initiating RNA replication), such that a stable duplex does not form between the template and primer in solution in the absence of HCV replicase. Formation of a stable duplex may prevent the replicase from binding the template/primer pair efficiently. The primer basepairs with the 3' terminus of the template in the presence of HCV replicase to form a catalytic complex (i.e., HCV polymerase, template and primer), which permits nucleotide incorporation into the primer by extension.

The present invention also provides quaternary complexes of NS5B/template/primer/nucleotide substrate, which can be used to establish a reliable replicase assay system for quantitatively studying the kinetics and mechanism of HCV NS5B-catalyzed nucleotide incorporation. By providing more effective binding of the template and primer to the polymerase active site, and thus permitting more efficient nucleotide incorporation, RNA templates and primers of the present invention are useful for developing more reliable and sensitive high-throughput screening assays for HCV polymerase inhibitors. Thus, the replicase complexes and screening assays of the present invention will permit: (1) establishment of sensitive RdRp assays to screen and evaluate antiviral inhibitors and to improve the specificity and efficacy of the inhibitors; (2) development of a reliable system to determine the kinetic and thermodynamic constants of HCV NS5B-catalyzed nucleotide incorporation; (3) investigation of mechanistic inhibitors for mis-incorporation or chain-termination; and (4) design of small RNA and primer for co-crystallization of binary, ternary and quaternary complexes, and subsequent co-crystallization with inhibitor compounds.

Thus, in one embodiment, the invention provides an HCV replicase complex comprising an HCV NS5B protein, a linear nucleic acid template of at least five nucleotides and a complementary nucleic acid primer of two or three nucleotides that anneals to the 3' terminus of the template, wherein the template and primer cannot form a stable duplex in solution in the absence of HCV NS5B protein.

In another embodiment, the present invention provides an assay system for HCV replicase activity, which comprises an RNA template that is at least five nucleotides and a short RNA primer (e.g., two or three nucleotides) that is complementary to the 3' terminus of the template, an enzymatically active amount of HCV NS5B protein, ATP, GTP, CTP, and UTP nucleoside triphosphates (NTPs), where the primer (or alternatively only one of the NTPs) is radiolabeled, and an assay buffer that supports replication activity of NS5B.

In yet another embodiment, the present invention provides a method for-detecting HCV replicase activity by detecting a nucleic acid synthesized by HCV NS5B using an assay system of the invention. Inhibitors of replicase activity can be identified using this method also.

Thus, it is an object of the invention to provide HCV replicase complexes comprised of unstable (in the absence of HCV replicase) template and primer pairs, and an assay system comprising the same, to characterize HCV replicase activity, e.g., mechanistic and kinetic activity.

These and other objects of the invention have been achieved, as described below in the following Detailed Description of the Invention and Example sections.

DETAILED DESCRIPTION OF THE INVENTION

All references cited herein are hereby incorporated by reference in their entireties.

This invention is based, in part, on the discovery of specific features of RNA templates and primer pairs that allow optimal, productive binding to the HCV replicase active site and subsequent incorporation of nucleotide, as detected by extension of the primers.

A large number of synthetic RNA template and primer pairs were tested for the ability of HCV replicase to effectively incorporate nucleotide substrate in a template dependent manner. The conventional, pre-annealed (stable) template-primer duplexes are poor substrates for directing nucleotide incorporation by HCV NS5B as demonstrated in the Example below. Several synthetic RNAs used in conventional replicase assays, either having five G:C basepairs or a stable tetraloop at the 3' end, were poor substrates of HCV and BVDV (a related pestivirus) polymerase enzymes. Instead, it was determined that RNA template-primer pairs of the present invention allow HCV replicase to efficiently extend a primer in a template-dependent fashion. Such template-primer pairs thus have the following features: (1) a small primer (preferably two or three bases) that does not form a stable duplex with a complementary template in solution under typical nucleic acid annealing conditions; (2) the primer basepairs with the 3' terminal end of the template; and (3) the template is three or more nucleotides (preferably five or more nucleotides).

General Definitions

The term "complementary" refers to a nucleic acid sequence that, when arranged in an, anti-parallel fashion with another nucleic acid sequence, forms Watsoni-Crick base-pairs. In particular, C and G bases pair together, and A and U bases pair together. G:C base pairs, which involve the formation of three hydrogen bonds, are stronger. The greater the number of G:C base pairs in complementary sequences, the higher the melting temperature ($T_m$) which is needed to denature (melt) the duplex region.

The terms "copy-back" or "elongation", and grammatical variations thereof, refer to a primer dependent mechanism for initiating RNA synthesis in a template-dependent fashion. As used herein, the term "de novo" refers to a primer independent mechanism for initiating RNA synthesis in a template-dependent fashion.

The term "assay system" refers to an experimental arrangement designed to measure NS5B activity. An assay system can be used with small molecule inhibitor compounds to determine HCV NS5B activity in its presence. Such inhibitors are discussed in greater detail below. An assay system can be in a high throughput mode, or an individual assay mode, depending for example on whether it is adapted for screening or for elucidating mechanisms of activity.

An "RNA template" is an oligonucleotide RNA, preferably prepared from ribonucleotides (since HCV NS5B does not use a DNA template efficiently), having a sequence that permits replication by NS5B. In a specific embodiment, the RNA template has a sequence similar to the 3' end of the HCV genome.

The term "stable duplex" refers to a double stranded RNA molecule that contains a template and primer bound when in solution under typical annealing conditions. The binding of a stable duplex has a Tm that is generally higher than 50° C. Generally, it is the length of the complementary region that determines the stability of the binding, with G and C pairs contributing to more stable binding.

An "unstable duplex" refers to a double stranded RNA molecule that contains a template and primer which bind weakly in solution (if at all), i.e., the Tm is less than 30° C., in the absence of HCV replicase enzyme. Thus, the binding is not stable under typical RNA annealing conditions. The length of the complementary region between the template and primer is preferably less than 5 basepairs, more preferably it is two or three basepairs, to provide such unstable binding.

An "HCV replicase complex" is an HCV NS5B polypeptide, which has bound to the replicase active site an RNA template and a primer complementary to the template, such that the binding is catalytically productive, i.e., it results in replication of the template by nucleotide incorporation into the template (elongation of the complementary-primer) Replication of RNA on a template by an RNA-dependent RNA polymerase such as HCV NS5B can be confirmed using methods well known in the art, and as described herein.

The terms "replication", "polymerization" and "transcription", and their grammatical variations, are used interchangably in connection with HCV NS5B in reference to HCV NS5B enzymatic activity.

A "nucleoside triphosphate " ("NTP") refers to a ribonucleotide substrate of HCV replicase. A radiolabel on a ribonucleotide triphosphate can be a phosphate isotope, e.g., $^{33}P$ or $^{32}P$. The isotope $^{32}P$ provides a stronger signal for detection. Other radioisotopes can also be used, including but not limited to tritium ($^{3}H$) and carbon 14($^{14}C$). Other types of labels are likely to interfere unacceptably with enzymatic activity and are therefore not desirable. Labeling of the α-P will result in incorporation of the label with each added NTP onto the elongated product. It is noted that, alternatively, the radiolabel may exist instead on the primer, rather than an NTP, to detect HCV replicase activity.

In a specific embodiment, the term "about" or "approximately" means within a statistically meaningful range of a value. Such a range can be within an order of magnitude, preferably within 20%, more preferably still within 10%, and even more preferably within 5% of a given value or range. The allowable variation encompassed by the term about or approximately depends on the particular system under study, and can be readily appreciated by one of ordinary skill in the art.

In accordance with the present invention there may be employed conventional molecular biology, microbiology, and recombinant DNA techniques within the skill of the art for the production of NS5B. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis [M. J. Gait ed. (1984)]; Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; A Practical Guide To Molecular Cloning [B. Perbal (1984)]; Current Protocols in Molecular Biology, John Wiley & Sons, Inc. [F. M. Ausubel et al. (eds.) (1994)].

HCV Replicase (NS5B)

The terms "NS5B", "replicase", "HCV polymerase" or "RNA-dependent RNA-polymerase" ("RdRp") refers to an NS5B enzyme encoded by an HCV NS5B gene, which exhibits RNA-dependant RNA polymerase activity. The ability of HCV NS5B to polymerize ribonucleotides may be referred to as "RNA-dependent" RNA polymerase, replicase, or enzymatic activity, which is well known in the art.

The NS5B gene product is encoded by a region near the 3' end of the HCV genome. For example, in the HCV-1apolyprotein [see, e.g., Behrens et al., EMBO J. 15:12–22 (1997)], it corresponds to amino acid residues 2420 to 3010. The NS5B protein has a molecular weight of 65 kD, and mediates both template dependent (RdRp) and template independent (TNTase) catalytic addition of ribonucleotides to the 3' termini of exogenous RNA in a $Mg^{2+}$-dependent process [see International Patent Publication WO 96137619; Lohmann et al., Virology 249:108–118 (1998)]. $Mn^{2+}$ can be substituted for $Mg^{2+}$, and appears to be the preferred cofactor [Ferrari et al., J. Virol. 73:1649–54 (1999)]. Thus, an assay buffer that supports replication activity (i.e., RNA polymerization or the catalytic addition of ribonucleotides to the 3' termini of exogenous RNA) requires a divalent cation such as $Mg^{2+}$ or $Mn^{2+}$. Gliotoxin inhibits HCV NS5B replicase in a dose dependent manner [Ferrari et al., supra].

HCV NS5B for use in an assay of the present invention can be obtained from any source, although recombinant production using conventional methods is preferred to ensure an adequate supply of the enzyme for study.

In a preferred embodiment, HCV NS5B is expressed in E. coli as a soluble product which lacks the hydrophobic C terminus and the tetraleucine motif responsible for the solubility profile of full-length NS5B [Ferrari et al., J. Virol. 73:1649–54 (1999)]. In this specific embodiment, a consensus NS5B sequence from HCV-1b can be cloned from a BK isolate. A computer intensive approach was used to identify the non-consensus mutations in NS5B of the BK isolate. The amino acid sequence of NS5B (BK) was compared to 16 NS5B proteins from different genotypes and subtypes. Four isolates representing genotype 1 subtype-a (HCV-1) and five from HCV-1b were used. The rest were from HCV-2a, 2b, 3a, 3b, 4a, 5a and 6a. Two potential non-consensus mutations were identified: T at position 329 and V at position 338 (numbered according to the sequence of unmodified NS5B). The corresponding amino acids in other isolates were V and A respectively, which are consensus (i.e., reflect the most frequently occurring or common amino acids at each position of HCV strains) among different genotypes. These mutations were likely introduced into the cDNA clones isolated during reverse transcriptase and polymerase chain reaction (RT-RCR). RT-PCR is a commonly used method to isolate HCV cDNA clones, but this methods lacks a proofreading process, which is required to prevent mis-incorporations (or errors) in the cDNA clones. Such mis-incorporations often result in mis-sense mutations at the amino acid level which may lead to functional defects in the protein products of HCV.

To repair these non-consensus mutations, site-directed mutagenesis using the "Quick Change" mutagenesis kit (Stratagene, Calif.) was performed. The sequence of the resulting clone was verified by direct sequencing; it represents the consensus clone of NS5B of the BK isolate. This approach of generating consensus clones has been proven to be essential for obtaining biologically and functionally active clones of HCV. The consensus NS5B was subcloned into pET-21b (Novagen) between NheI and BamHI sites. Two codons were engineered at the N-terminus, coding for the amino acids "MA", replacing the native amino acids "SM" at the N-terminus of NS5B. The C-terminal 21 amino acids were removed to improve the solubility (Ferrari et al., 1999, *supra*). A polyhistidine tag was engineered to replace the C-terminal domain to facilitate the purification of the enzyme.

Alternatively, a PCR product containing the cDNA region encoding amino acids 2420–3010 of the HCV polyprotein (the NS5B protein) can be cloned into a vector, such as between the BamHI and HindIII sites of the pBlue BacIII vector (Invitrogen, California), and expressed in Sf9 cells by a baculovirus vector [International Patent Publication WO 96/37619; Behrens et al., EMBO J. 15:12–22 (1996)]. A baculovirus expression system can also be used to express a C-terminal, histidine-tagged NS5B construct [Lohlnann et al., J. Virol. 71:8416–28 (1997)].

In addition to the preferred consensus NS5B described above, various mutant forms, homologues and variants of NS5B can be employed. The terms "mutant" and "mutation" mean any detectable change in genetic material, e.g. DNA, or any process, mechanism, or result of such a change. This includes gene mutations, in which the structure (e.g., DNA sequence) of a gene is altered, any gene or DNA arising from any mutation process, and any expression product (e.g., protein) expressed by a modified gene or DNA sequence. The term "variant" may also be used to indicate a modified or altered gene, DNA sequence, enzyme, cell, etc., i.e., any kind of mutant. "Sequence-conservative variants" of NS5B are those in which a change of one or more nucleotides in a given codon position results in no alteration in the amino acid encoded at that position. "Function-conservative variants" of NS5B are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Both sequence- and function-conservative variants of HCV NS5B are contemplated for use in the present invention.

Protein or polypeptide homology, or sequence identity, is determined by optimizing residue matches, if necessary, by introducing gaps as required. See, e.g., Needleham, et al. (1970) *J. Mol. Biol.* 48:443–453; Sankoff, et al. (1983) chapter one in *Time Warps String Edits. and Macromolecules: The Theory and Practice of Sequence Comparison,* Addison-Wesley, Reading, Mass.; and software packages from IntelliGenetics, Mountain View, Calif.; and the University of Wisconsin Genetics Computer Group (GCG), Madison, Wis. (each incorporated herein by reference). This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are intended to include natural genotypic or isolate variations of the NS5B amino acid sequence. Typical homologous NS5B polypeptides used in this invention will have from 50–100% homology (if gaps can be introduced), to 60–100% homology (if conservative substitutions are included), e.g., with HCV-1a NS5B. Homology measures will be at least about 70%, generally at least 76%, more generally at least 81%, often at least 85%, more often at least 88%, typically at least 90%, more typically at least 92%, usually at least 94%, more usually at least 95%, preferably at least 96%, and more preferably at least 97%, and in particularly preferred embodiments, at least 98% or more. The degree of homology will vary with the length and number of NS5B polypeptides compared.

RNA Template and Primer

The present invention provides an optimized RNA template for HCV NS5B replication assays. Small viral RNAs used in the conventional replication assays were found inefficient in supporting RNA synthesis. However, use of an RNA template and primer pair of the present invention in screening assays, as discussed in greater detail below, is useful for determining the kinetic, thermodynamic and mechanistic properties of NS5B replication, and ultimately in the development of inhibitors of NS5B.

An RNA template of the present invention is at least three nucleotides long, more preferably it is at least five nucleotides long (longer templates, e.g., 40 to 50 nucleotides can be employed as desired), and has unstable, weak basepairing with a complementary primer at the 3' terminus of the template. The 3' terminus of the template is preferably linear, e.g., free of any secondary structures. For example, a template having a stable tetraloop at the 3' end fails to support RNA synthesis and is undesirable.

A primer of the present invention can be from 2 to 5 nucleotides in length, most preferably a di- or tri-nucleotide, in order to achieve optimum nucleotide incorporation into the template. The primer is complementary to the 3' terminus of the template. Various dinucleotides can be used as a primer of the present invention (with varying primer efficiency), e.g., pGpG~pGpC>pCpG>pCpC~pGpU>pUpG, where pGpG is more efficient than pUpG, and "~" denotes about the same efficiency. Thus, examples of preferred primer sequences that can be used with the invention include: GG, GC, CG, CC, GU, UG, CA, AC. Trinucleotides such as GGG and GCG are also useful as primers. It is preferred that the first base of a primer of the invention is a guanine. Trinucleotide primers can be designed using the rationale described. The sequences GGGG (SEQ ID NO: 32) and GGGGG (SEQ ID NO: 33) can also be used as primers, but have a reduced efficiency for nucleotide incorporation in comparison with di- and tri- nucleotide primers.

A template and primer of the present invention will not form a stable duplex in solution in the absence of HCV NS5B replicase. Upon binding of the template to the active site of HCV NS5B replicase, the primer can basepair at the complementary 3' terminus of the template. The primer can then be extended by the replicase enzyme. Thus, template-primer pairs of the present invention form an unstable duplex, if at all, in the absence of HCV NS5B; the replicase enzyme therefore stabilizes the basepairing of the template RNA with the complementary primer.

Generally, a stable duplex is produced if a template and a primer form more than 6 consecutive G:C basepairs between them having a Tm of greater than 30° C. The more basepairs formed between the template and primer, the more stable the duplex is. Therefore, it is preferred that the complementary region between the primer and template is from two to five consecutive bases, to ensure the duplex is unstable.

Templates and primers of the present invention can be prepared synthetically, e.g., on a nucleic acid synthesizer. RNA templates and primers can also be obtained from commercial sources (Oligos Etc., Inc., Wilsonville, Oreg.; Dharmacon Research, Inc., Boulder, Colo.; HHMI Biopolymer/Keck FBRL, Yale University, New Haven, Conn.; Baron Biotech, Milford, Conn.).

NS5B Activity Assays

Generally, NS5B polymerase activity assays must be performed under conditions that permit polymerization. For assays of the present invention, a divalent cation, e.g., $Mg^{2+}$ or $Mn^{2+}$ (as described above), sufficient quantities of ribonucleotide triphosphates to serve as substrates for the polymerase, an RNA template and complementary primer of the invention, and HCV NS5B in an isotonically buffered aqueous solution are needed. The assay can be performed in a buffer containing, e.g., 50 mM HEPES, pH 7.3, 5 mM $MgCl_2$, 50 mM NaCl, 10 $\mu$M β-mercaptoethanol, 100 $\mu$M NTP (i.e., ATP, CTP, GTP, UTP), 5 $\mu$M RNA template, 10 $\mu$M end-labeled primer (e.g. $^{33}$pGpG), and 3 to 5 $\mu$M of HCV NS5B protein. Any label can be used for the primer, but preferably it is a phosphorous isotope, e.g., $^{33}P$ or $^{33}P$. Alternatively, it may be preferable to label an NTP instead of the primer. Reagents used in a replicase assay can be substituted for those that have similar properties in a replicase assay system without departing from the spirit of the invention. The concentrations of reagents can also be varied as needed.

The polymerase reaction can be performed at 30° C., although higher and lower temperatures are permissible. For example, other polymerases are more efficient at 37° C. The reaction time can vary, depending on the rate of product formation, but should be long enough to permit at least one complete round of synthesis.

In one embodiment, reactions can be performed in the presence of candidate inhibitory compounds. Such compounds are useful, e.g., to evaluate their ability to inhibit NS5B activity. HCV NS5B inhibitory compounds, which can be identified in a primary screen, e.g., by the ability to bind to NS5B or to inhibit NS5B activity (in a primer-dependent fashion), are good lead candidates for developing anti-HCV pharmaceuticals.

As used herein, the term "inhibitory compound" refers to any molecule or complex of more than one molecule, which decreases or inhibits HCV NS5B enzymatic function. The present invention contemplates screens for synthetic small molecule agents, chemical compounds, chemical complexes, and salts thereof as well as screens for natural products, such as plant extracts or materials obtained from fermentation broths.

In activity assays of the present invention, compounds with known replicase inhibitory activity can be used as positive controls. One example of such a compound is gliotoxin, which is a known poliovirus 3D RdRp inhibitor. Other such compounds include nucleotide analogs, such as dideoxy nucleotides, that inhibit nucleic acid synthesis.

High Throughput-primary Screens

In one embodiment, a replication assay system of the invention can be formatted in an automated high throughput screen (HTS) for primary screening of candidate anti-HCV NS5B compounds.

One example of a HTS screen of the invention is scintillation proximity assay (SPA). In such an assay, the primer RNA may be biotinylated (e.g., at the 5' end) and the synthesized products are captured onto streptavidin-coated SPA beads. [Ferrari et al., J. Virol. 73:1649–54 (1999)]

Secondary/Mechanism Screens

While the discovery of the optimized RNA template and primer features for NS5B replication provides for primary screening assays, particularly in an HTS format, a more important application of the present invention is use of the HCV replicase activity as a probe for mechanistic studies of candidate compounds discovered in a primary screen. In particular, the discovery that HCV NS5B uses a template having a linear 3' terminus and a short complementary primer more efficiently than conventional template-primer pairs for HCV NS5B, provides a better means for identifying NS5B inhibitory compounds that directly interfere with the replication process, e.g., prevent or slow primer extension or block template and primer from forming a complex in the polymerase active site. A candidate compound that has been identified using replicase complexes of the present invention may be more effective than replication inhibitors discovered using other HCV assay systems previously known in the art, because the former specifically targets a highly efficient HCV replication complex.

The replication assays described in greater detail in the Example provide a means to further evaluate NS5B activity. These assays can be readily adapted for dose response or absolute (saturation) inhibition by potential anti-HCV NS5B compounds. For example, an assay system comprising 50 mM HEPES, pH 7.3, 5 mM $MgCl_2$, 50 mM NaCl, 10 $\mu$M β-mercaptoethanol, 100 $\mu$M NTP, 5 $\mu$M of RNA template, 10 $\mu$M end-labeled primer (e.g., $^{33}$pGpG), and 3 to 5 $\mu$M of HCV NS5B protein, can be used in the presence and absence of a dilution series of candidate inhibitory compounds. The ability of such compounds to inhibit replication initiation, nucleotide incorporation or elongation can be detected, e.g., by running the reaction for about 30 minutes, extracting the products by phenol/chloroform extraction and ethanol precipitation, separating the nucleic acids on a 23 to 25% PAGE gel in 6M urea, and detecting products by autoradiography. Alternatively, a membrane binding assay in which the radiolabeled products are captured to a membrane may be used as the assay format.

EXAMPLE

In this Example, the template requirements for in vitro RNA replication directed by HCV N-S5B are provided. In the case of intramolecular copy-back RNA synthesis, small synthetic RNAs with a stable stemloop at the 3' terminus were poorly utilized by HCV NS5B. Instead, the HCV replicase preferred RNA having an unstable, single-stranded terminus, which suggests that a stable, pre-annealed double-stranded template-primer pair cannot efficiently access the active site of the enzyme. Therefore, a number of template and primer pairs with different basepairing strength and length were tested for directing RNA synthesis. It was discovered that small primers (e.g., 2 to 3 nucleotides) are highly efficient in priming RNA synthesis, as detected by extension of end-labeled primers. This finding is expected to facilitate the establishment of an in vitro system to quantitatively analyze the transient kinetics and thermodynamics of nucleotide incorporation directed by HCV NS5B.

Materials and Methods

Protein expression and purification. DNA sequences encoding HCV, BVDV and polivirus (PV) RdRp proteins were cloned in a bacterial expression vector (pET). To improve solubility of HCV and BVDV NS5B proteins, the C-terminal hydrophobic regions (21 amino acids for HCV and 19 for BVDV), were removed [Ferrari et al., J. Virol. 73: 1649–1654 (1999); Lai et al., J. Virol. 73: 10129–10136 (1999)]; sequences coding for a methionine at the N-terminus and a polyhistidine tag at the C-terminus were inserted to facilitate the cloning, expression and purification. Protein production was induced in freshly transformed E.coli JM109 (DE3) cell, at 0.6 OD 600 mn, by isopropyl thio-β-D-galactoside (IPTG) at a final concentration of 0.2 mM. Soluble cell lysates were batch-adsorbed onto a nickel-chelated (Ni-NTA) column. After extensive washes (10 column volumes) under a high concentration of salt (1M NaCl), the protein was eluted off the column with a buffer containing 0.3 M imidazole. The protein was further purified using a Superdex-200 gel-filtration column (Pharmacia Biotech, Piscataway, N.J.). Fractions from the gel-filtration column were subjected to sodium dodecyl sulfate-polyacrylamide gel electrophoresis (SDS-PAGE).

TABLE

Templates Tested For Replicase Activity

| Sequence | ID |
|---|---|
| 5' GGA AAA AAA AAA AAA AAA AAA AAA AAA AAA AAA AAA 3' | (SEQ ID NO:2); |
| 5' GGA AAA AAA AAA AAA AAA AAA AAA AAA AAA AAA AAU 3' | (SEQ ID NO:3); |
| 5' GGA AAA AAA AAA AAA AAA AAA AAA AAA UAU AUA UAU 3' | (SEQ ID NO:4); |
| 5' GGA AAA AAA AAA AAA AAA AAA AAA AAC GCG CGC GCG 3' | (SEQ ID NO:5); |
| 5' GCA UGG GCC C 3' | (SEQ ID NO:6); |
| 5' GCCCCC GCCCCC GCCCCC GCCCCC GCCCGC 3' | (SEQ ID NO:7); |
| 5' G UGG 3' | (SEQ ID NO:8); |
| 5' UCC UCC UCC UCC UCC UCC UCC 3' | (SEQ ID NO:9); |
| 5' GCC GCC GCC GCC GCC GCC GCC 3' | (SEQ ID NO:10); |
| 5' ACC ACC ACC ACC ACC ACC ACC 3' | (SEQ ID NO:11); |

TABLE-continued

Templates Tested For Replicase Activity

| | |
|---|---|
| 5' GCCC GCCC GCCC GCCC GCCC GCCC 3' | (SEQ ID NO:12); |
| 5' GCCCC GCCCC GCCCC GCCCC GCCCC 3' | (SEQ ID NO:13); |
| 5' AAA AAA AAA AAA AAA CAG UCC 3' | (SEQ ID NO:14); |
| 5' AAA AAA AAA AAA CAG UCC 3' | (SEQ ID NO:15); |
| 5' AAA AAA AAA CAG UCC 3' | (SEQ ID NO:16); |
| 5' AAA AAA CAG UCC 3' | (SEQ ID NO:17); |
| 5' AAA CAG UCC 3' | (SEQ ID NO:18); |
| 5' A CAG UCC 3' | (SEQ ID NO:19); |
| 5' AG UCC 3' | (SEQ ID NO:20); |
| 5' AAA AAA CAG UGC 3' | (SEQ ID NO:21); |
| 5' AAA AAA CAG UCG 3' | (SEQ ID NO:22); |
| 5' AAA AAA CAG UGG 3' | (SEQ ID NO:23); |
| 5' AAA AAA CAG UAC 3' | (SEQ ID NO:24); |
| 5' AAA AAA CAG UCA 3' | (SEQ ID NO:25); |
| 5' UCU GCA GAU CAU GU 3' | (SEQ ID NO:26); |
| 5' AUC AGG GGG CUG GC 3' | (SEQ ID NO:27); |
| 5' UCC UCC UCC UCC UCC UCC AAA 3' | (SEQ ID NO:28); |
| 5' CAG UCC 3' | (SEQ ID NO:29); |
| 5' CC ACC ACC ACC ACC ACC ACCA 3' | (SEQ ID NO:30); |
| 5' C ACC ACC ACC ACC ACC ACC AC 3' | (SEQ ID NO:31). |

RNA replication assays. A 40-nt synthetic RNA (5' AAA AAA AAA AAA AAA AAA AAA AAA AAA AGG ACU UCG GUC C 3'; SEQ ID NO: 1) having a stable tetraloop at the 3' terminus, and four short synthetic RNAs (SEQ ID NOS: 2–5), having different 3' terminal sequences, were used as templates in a copy-back RNA replication assay by HCV, BVDV and PV replicases. Standard reactions for HCV NS5B (in a volume of 40 µl) contained 20 mM HEPES, 7.5 mM DTT, 50 mM NaCl, 5 mM MgCl$_2$ or MnCl$_2$, 0.05% glycerol, 0.2–0.5 µM of RNA template, 100 µM of UTP and CTP, 10 µCi of α-$^{33}$p-UTP label and 300 ng of HCV NS5B. Reaction conditions for BVDV NS5B and PV 3Dpol are as described previously [Lai et al., J. Virol. 73:10129–10131 (1999); Plotch et al., J. Virol. 63: 216–225 (1989)].

In addition, the RNA template of SEQ ID NO: 4 was tested for template usage, each reaction containing 0.2 µM of end-labeled template, 100 µM each of UTP and CTP, and 0, 4 or 20 µM HCV NS5B protein. For pre-annealed syn/sub RNA (SEQ ID NO: 6), each reaction contained 0.5 µM of end-labeled sym/sub RNA, 100 µM of ATP and 0 or 5 µM of HCV or PV polymerase protein. All reactions were performed at 30° C. for 30 min and terminated by phenol and chloroform extraction. Labeled product was precipitated with ethanol in the presence of glycogen carrier. The pellet was dissolved in-DEPC-treated water and resolved in a 15% PAGE/Urea/TBE gel (Novex, San Diego, Calif.) according to the manufacturer's instructions. After electrophoresis, the gel was fixed, vacuum dried and subjected to autoradiography.

End-labeling of small RNA template or primer. Synthetic RNA templates and primers were chemically synthesized (Oligos, Etc.,Wilsonville, Oreg.). The RNAs were all gel purified except for those containing fewer than 7 nucleotides. End labeling of RNA template or primer was performed using T4 polynucleotide kinase and γ-$^{33}$P-ATP. Labeling reactions were carried out at 37° C. for 30 min in a 50 µl volume containing 50 pmoles of RNA, 100 µCi of γ-$^{33}$P-ATP and 10 units of T4 polynucleotide kinase. After labeling, the reaction mixture was extracted with phenol and chloroform and precipitated with ethanol in the presence of glycogen as carrier. The labeled RNA was dissolved in DEPC-treated water to required concentrations.

Nucleotide incorporation assay using end-labeled primers. A standard nucleotide incorporation reaction was performed in a 20 µl volume, containing 50 mM HEPES (pH 7.3), 10 mM β-mecaptoethanol, 50 mM NaCl, 5 mM MgCl$_2$, 5 µM of template RNA, 10 µM of end-labeled primer, 3 to 5 µM of polymerase protein and 100 µM of NTP substrate, as described. Single nucleotide incorporation by HCV replicase was tested using radiolabeled diguanylate ($^{33}$pGpG) as a primer and three RNA templates corresponding to SEQ ID NO: 11 [(ACC)$_7$], SEQ ID NO: 9 [(tJCC)$_7$], and SEQ ID NO: 10 [(GCC)$_7$]. Reactions involved $^{33}$pGpG primer alone and with (1) (ACC)$_7$ RNA as the template plus either no NTP, 100 µM UTP or 100 µM ATP, (2) (UCC)$_7$ RNA as the template plus either no NTP, 100 µM ATP or 100 µM CTP, and (3) (GCC)$_7$ RNA as the template plus either no NTP, 100 µM CTP or 100 µM ATP. To show the efficiency of guanylate primers of different length in priming nucleotide incorporation, four template-primer pairs were tested in a standard primer-extension assay: GCCGCCGCCGCCGC-CGCCGCC (SEQ ID NO: 10)/$^{33}$pGG; GCCCGCCCGC-CCGCCCGCCCGCCC (SEQ ID NO: 12)/$^{33}$pGGG; GCCCCGCCCCGCCCCGCCCCGCCCC,(SEQ ID NO-13)/$^{33}$pGGGG (SEQ ID NO: 32); and GCCCCCGC-CCCCGCCCCCGCCCCCGCCCCC (SEQ ID NO: 7)/$^{33}$pGpqGG (SEQ ID NO: 33). Reactions were performed using 100 µM of CTP or without a nucleotide substrate.

To demonstrate that a primer of the invention must basepair to the 3' terminus of an RNA template of the invention template activity was tested using SEQ ID NO: 28 "(UCC)$_6$AAA" or SEQ ID NO: 9 "(UCC)$_7$" as templates. Reactions contained (UCC)$_7$ alone, (UCC)$_7$ plus 100 µM of ATP, (UCC)$_6$AAA alone, or (UCC)$_6$AAA plus 100 µM of ATP. In addition, RNAs of SEQ ID NOS: 11, 30 and 31 were tested for single-nucleotide incorporation with $^{33}$pGpG as the primer.

To show the minimum length requirement for a template RNA of the invention RNA templates of decreasing length (21 to 4-nt), e.g., SEQ ID NOS: 8 and 14–20 were tested for the ability to direct single-nucleotide incorporation using $^{33}$pGpG as the primer. All reactions contained 100 µM of ATP and one template RNA. Multiple cycles of nucleotide incorporation were performed using a 10-mer RNA and $^{33}$pGpG as the primer. Reactions contained either 100 µM of ATP alone, or 100 µM each of ATP and CTP, or 100 µM each of ATP, CTP and GTP. The reactions were quenched at different times from 15 to 900 seconds.

Various dinucleotide primers for RNA synthesis and nucleotide incorporation using HCV 3' terminal sequences as template were used. The following RNA templates were used: 5' AAAAAACAGUCC 3' (SEQ ID NO: 17), 5' AAAACAGUGC 3' (SEQ ID NO: 21), 5' AAAAAA-CAGUCG 3' (SEQ ID NO: 22), 5' AAAAAACAGUGG 3' (SEQ ID NO: 23), 5' AAAAAACAGUAC 3' (SEQ ID NO: 24), 5' AAAAAACAGUCA 3' (SEQ ID NO: 25), which differ by two residues at the 3' terminal positions. Dinucleotide primers, $^{33}$pGpG, $^{33}$pGpC, $^{33}$pCpG, $^{33}$pCpC, $^{33}$pGpU and $^{33}$pUpG, were paired with respective templates in the absence or presence of 100 μM ATP substrate. RNA templates, 3'(+) and 3'(−), consisted of the 3' terminal sequences of positive-strand and negative-strand HCV genome, respectively. Primers $^{33}$pApC and $^{33}$pGpC were used for 3'(+) and 3'(−) RNA, respectively, in the absence of nucleotide substrate and in the presence of ATP or CTP.

Reaction mixtures were incubated at 30° C. for 30 min, followed by phenol and chloroform extraction and ethanol precipitation in the presence of glycogen carrier. Product was dissolved in a urea/TBE sample buffer (Novex, San Diego, Calif.) and separated on a 23 to 25% PAGE/6 M Urea/1× TBE gel. The gel was then covered with plastic wrap and exposed to an X-ray film.

Results

Copy-back RNA synthesis using a template with a stable tetraloop at the 3'end. Based on previous reports, viral replicases, including HCV NS5B, are capable of using RNA templates that fold back intramolecularly at the 3' terminus to produce a near dimer-size hairpin product via a copy-back mechanism. To test whether HCV NS5B can use a small synthetic RNA of defined sequence as template for copy-back RNA synthesis, a 40-nt RNA (5'- A$_{28}$GGACUUCG GUCC3'; SEQ ID NO: 1) which forms a stable tetraloop through the underlined complementary sequence at the 3' terminus was synthesized [Antao et al., Nucl. Acid Res. 19: 5901–5905 (1991); Nucl. Acid Res. 23: 3056–3063 (1995)]. This tetraloop has a calculated melting temperature ($T_m$) of about 71° C. For comparison, replicase enzymes from poliovirus (PV 3D$^{pol}$) and bovine viral diarrhea virus (BVDV NS5B) were prepared and tested in parallel with HCV NS5B. Only PV 3DP$^{pol}$ was able to use the tetraloop efficiently as the copy-back primer, and produced a near dimer-size hairpin product. In contrast, little activity was detected for HCV or BVDV NS5B. The lack of product formation by HCV and BVDV NS5B was not due to insufficient amounts of enzyme used in the reactions, since the RdRp activity for each polymerase was normalized using a standard scintillation proximity assay (SPA) (Ferrari et al., 1999, supra). These results suggest that flaviviral RdRps might require different features at the 3' terminus of the template for copy-back RNA replication.

HCVNS5B utilized RNA with an unstable stemloop at the 3'terminus. To identify the specific template requirement for copy-back RNA synthesis by HCV NS5B, four synthetic RNAs with different 3' terminal sequences were tested. Two of these templates corresponding to SEQ ID NO: 2, having "AA" at the 3' terminus, and to SEQ ID NO: 3, having "AU" at the 3' terminus, were unable to form stemloops. The other two templates formed either a weak stemloop (SEQ ID NO: 4, having "(AU)$_5$" at the 3' terminus) or a relatively stable stemloop (SEQ ID NO: 5, having "(CG)$_5$" at the 3' terminus) at the 3' terminus.

The results demonstrate that all three viral polymerases fail to produce any product when using templates having "AA" at the 3' terminus. This indicates a lack of terminal transferase activity for these polymerases using this type of template. Weak RNA synthesis was detected for BVDV and HCV NS5B when templates having an "AU" sequence at the 3' terminus were employed, probably resulting from remote basepairing between the terminal uridylate and an internal adenylate. All three viral replicase enzymes exhibited copy-back activity and produced a near dimer-size hairpin products when using templates having an "(AU)$_5$" sequence at the 3' terminus. This indicates that the alternating "A-U" basepairs at the 3' terminus were able to support copy-back RNA synthesis. Replacement of the alternating "A-U" basepairs with "C-G" basepairs significantly reduces the RdRp activity for both HCV and BVDV NS5B. This observation suggests that a more stable copy-back primer at the D' terminus (formed by the stronger basepairing between the C and G bases) is detrimental to the copy-back RNA synthesis directed by flaviviral replicase enzymes. In contrast, this more stable copy-back primer-in-template "(CG)$_5$" enhanced the activity of PV 3D$^{pol}$, suggesting that PV 3D$^{pol}$ prefers a more stable stemloop as the copy-back primer. These results indicate that HCV NS5B polymerase prefer a template that has a very weak or no stemloop structure at the 3' terminus, but has the ability to fold back intramolecularly upon binding to the polymerase for copy-back RNA synthesis.

Poor template utilization by HCVNS5B. Efficient assembly of polymerase-RNA template/primer complexes that permit nucleotide incorporation is an essential step in determining the kinetics and mechanism of HCV NS5B-catalyzed RNA synthesis. The experiments described were performed in the presence of unlabeled template RNA and radiolabeled NTP substrate (α-$^{33}$P-JTP). Thus, the polymerase activity was measured based on the incorporation of radiolabeled UMP into the nascent RNA product. However, this type of assay did not reveal the proportion of RNA substrates bound productively by the enzyme to form the catalytically competent complexes. To address this issue, radiolabeled RNA templates (in the case of copy-back RNA synthesis) or primers (in the case of bi-molecular primer-dependent RNA synthesis) were used so that the proportion of the radiolabeled RNA substrates that were extended due to incorporation of unlabeled nucleotides can be easily determined. When an end-labeled template having a 3' terminus "(AU)$_5$" and unlabeled nucleotides (NTPs) were tested in the RdRp assay, the amount of the template RNA which was extended or utilized by HCV NS5B was too low to be detected, even when molar excess HCV NS5B was employed. As a control, the preannealed sym/sub RNA (SEQ ID NO: 6), which is an efficient template/primer pair for PV 3D$^{pol}$ [Arnold and Cameron, J. Biol. Chem. 275: 5329–5336 (2000)] was also tested. PV 3D$^{pol}$ efficiently utilized this duplex RNA and catalyzed template-dependent single nucleotide incorporation. However, no primer extension was observed in reactions containing HCV NS5B. These results revealed that only a very small portion of the template and primer was assembled correctly in the active site of HCV NS5B (i.e., forming the enzyme-substrate complexes competent for catalysis). The products generated in these reactions were detectable only by incorporation of radiolabeled nucleotides. This poor efficiency of properly assembling the template/primer in the active site of HCV NS5B prevented quantitative measurement of single nucleotide incorporation, which is required for kinetic analysis of NS5B-catalyzed polymerization reaction.

Dinucleotide primer initiates RNA synthesis efficiently. The previous results revealed that a stable stemloop at the 3' terminus of the RNA template or a pre-annealed RNA duplex prevents productive binding or proper entry of the RNA into the polymerase active site. The inability of HCV NS5B to utilize these substrates efficiently suggests unique structural elements interfere with the entry of double-stranded RNA molecules in the absence of conformational changes [Bressanelli et al., Proc. Natl. Acad. Sci USA 96:13034–13039 (1999); Lesburg et al., Nat. Struct. Biol. 6: 937–943 (1999)]. As demonstrated by the present invention, the correct docking of RNA to HCV NS5B requires a single-stranded 3' terminus of the template RNA. To show this, a series of templates and short primers were designed and evaluated. These short RNA primers do not form stable duplexes with the template RNA in solution, and therefore will not interfere with the template docking to the active site of NS5B. Once a template enters the polymerase active site correctly, a short primer may access the catalytic center independently and prime RNA synthesis from the bound single-stranded template RNA.

Three 21-nt RNAs containing the trinucleotide repeats "(ACC)$_7$" (SEQ ID NO: 11), "(UCC)$_7$" (SEQ ID NO: 9), and "(GCC)$_7$" (SEQ ID NO: 10) were tested for their ability to direct RNA synthesis using the end-labeled diguanylate ($^{33}$pGpG) primer. These templates were designed to: (1) avoid formation of stable secondary structure; (2) maximize the basepairing capability with the pGpG primer; and (3) allow detection of single nucleotide incorporation [UMP, AMP and CMP incorporation for (ACC)$_7$, (UCC)$_7$ and (GCC)$_7$, respectively]. Each reaction contained either no NTP or an indicated NTP substrate. Single nucleotide incorporation was monitored by the migration shift of the radiolabeled primers (from P to P+1). In the case of (ACC)$_7$, single nucleotide incorporation was observed only when UTP was used as the nucleotide substrate. Similar results were observed for template (UCC)$_7$ or (GCC)$_7$, in which only the correct nucleotide, ATP or CTP, resulted in primer extension. The results demonstrated that HCV NS5B was able to utilize a significant portion of the RNA template/primer and catalyze the template-dependent nucleotide incorporation. Under the reaction conditions employed, approximately 20–30% of the labeled primers were utilized by the polymerase, which is comparable to the extent of sym/sub RNA (SEQ ID NO: 6) utilization by PV 3D$^{pol}$ under similar reaction conditions.

Optimal length of the primer. To determine the optimal length of the guanylate primer that allows efficient nucleotide incorporation, four template and primer pairs were synthesized [(GCC)$_7$ (SEQ ID NO: 10)/$^{33}$pGpG; (GCCC)$_6$ (SEQ ID NO: 12)/$^{33}$pGGG; (GCCCC)$_5$ (SEQ ID NO: 13)/$^{33}$pGGGG (SEQ ID NO: 32); and (GCCCCC)$_5$ (SEQ ID NO: 7)/$^{33}$pGGGGG, (SEQ ID NO: 33)] in which the length of the primer, as well as the complementary sequence in the template RNA, varied from 2 to 5 nucleotides. Di- and tri-guanylate primers supported nucleotide incorporation with the highest efficiency. Further increases in primer length to 4 and 5 nucleotides were detrimental to the activity. Therefore, the diguanylate primer was chosen to further characterize this system.

The primer preferred to basepair with the 3'terminus of the template. The RNA templates tested could basepair with the diguanylate primer ($^{33}$pGG) at both 3' terminal and internal positions. To determine whether the polymerase initiated RNA synthesis from the 3'terminus or from an internal location, a new RNA template was designed in which the three terminal nucleotides of template (UCC)$_7$ (SEQ ID NO: 9) was modified from "UCC" to "AAA", i.e., (UCC)$_7$AAA (SEQ ID NO: 27). This modification rendered the RNA incapable of basepairing with pGpG primer at the terminal bases. When this RNA was tested, little nucleotide incorporation was detected, suggesting that the primer preferred to basepair with the 3' terminus of the template RNA to initiate RNA synthesis.

To further define the positional requirement, the sequence of the template RNA (SEQ ID NO: 11) was further modified such that one or two additional nucleotides were added to the 3' terminal dicytidylates (CC). The template bases "CC" were no longer terminally located. Accordingly, one or two residues were removed from the 5' terminus to retain the same template length. When these newly modified RNA templates (SEQ ID NOS: 30 and 31), were tested in the nucleotide incorporation assay, a significant reduction in activity was observed, further confirming that the primer preferred to basepair with the template at the 3' terminus in order to assemble catalytically competent complexes with the enzyme.

Minimal template length requirement for RNA synthesis. As demonstrated earlier, the primer preferred to basepair with the 3' terminus of the template RNA for nucleotide incorporation. The minimal length of the template required for this interaction was determined by designing a series of synthetic RNA templates, consisting of two cytidylates (CC) at the 3' terminus (for basepairing with the $^{33}$pGpG primer), a heterogeneots sequence (CAGU) in the middle and a stretch of adenylate of varying lengths at the 5' end: These templates ranged from 4 to 21 nucleotides in length (i.e., SEQ ID NOS: 8 and 14–20). Efficient nucleotide incorporation was observed with the template as short as 5-nt long. However, when the template was shortened to 4-nt, a significant reduction in nucleotide incorporation was observed. These results demonstrated that the minimal length of the template RNA was around 5-nucleotide for retaining sufficient template activity. Smaller templates might lack sufficient interaction with the enzyme to support initiation of RNA synthesis.

Use of dinucleotide other than pGpG to prime RNA synthesis. The above experiments were performed by using the $^{33}$pGG primer. To determine whether this could apply to other primer sequences, a series of 12-nt templates with variations at the 3' terminal positions (5'-AAAAAACAGU XY-3', where X and Y are variable nucleotides) (SEQ ID NOS: 17, 21–25) were tested along with the matching dinucleotide primers (pGpG, pGpC, pCpG, pCpC, pGpU or pUpG). All of the dinucleotides were capable of priming nucleotide (AMP) incorporation. The relative order of primer utilization efficiency was as follows: pGpG~pGpC>pCpG>pCpC~pGpU>pUpG. HCV NS5B seemed to prefer primers with a guanylate (G) at the 5'terminus.

Finally, whether HCV-derived RNAs could serve as the templates for dinucleotide-primed RNA synthesis was tested. For this purpose, RNAs (SEQ ID NOS 26 and 27), corresponding to the 3' terminus of HCV positive-strand and negative-strand RNA genomes were synthesized. When these RNAs were tested in the presence of appropriate endlabeled primer and NTP substrate [$^{33}$pApC and ATP for RNA corresponding to SEQ ID NO:26; $^{33}$pGpC and CTP for RNA corresponding to SEQ ID NO: 27, single-nucleotide incorporation was detected for both RNA templates though with different efficiencies. RNA corresponding to SEQ ID NO: 27 clearly possessed a higher overall activity than RNA corresponding to SEQ ID NO:26. Whether or not the dinucleotide-initiated RNA synthesis occurs in vivo can only be addressed in the context of a viral infection. Nonetheless, the observation that pGpC primed RNA synthesis from 3'(−) RNA corresponding to SEQ ID NO: 27 more efficiently than pApC from 3'(+) RNA corresponding to SEQ ID NO: 26 was consistent with the asymmetric synthesis of positive-strand RNA genome versus negative-strand RNA genome during viral replication.

Discussion

Several reports attempt to characterize the enzymatic activity of HCV NS5B [Behrens et al., EMBO J. 15: 12–22 (1996); De Francesco et al., Methods Enzymol. 275:,58–67 (1996); Ferrari et al., J. Virol. 73: 1649–1654 (1999); Lohmann et al., J. Virol. 71: 8416–8428 (1997)]. However, characterization of the reaction pathway of NS5B-catalyzed nucleotide incorporation was hindered in part due to the lack of template/primer pairs capable of efficiently assembling catalytically competent complexes with the enzyme. This Example, demonstrates that stable, pre-annealed, double-stranded RNAs are poor substrates for HCV NS5B. Instead, HCV polymerase efficiently utilizes short RNA primers, 2 to 3 nucleotides in length, to prime nucleotide incorporation, which can be followed by extension of radiolabeled primers. Furthermore, initiation of RNA synthesis preferentially occurs from the 3' terminus of the template RNA, suggesting that the replicase assembles at the 3' terminus of viral RNA. Consistent with this was the finding that both 3' termini of HCV (+)-strand and (−)-strand RNAs serve as templates for dinucleotide-primed RNA synthesis.

Recent structural studies revealed that HCV NS5B has a fully encircled active site with a relatively rigid interdomain structure, resembling the "closed" or "elongative" conformation of several other polymerases [Bressanelli et al., Proc. Natl. Acad. Sci USA 96:13034–13039 (1999); Ago et al., Structure 7: 1417–1426 (1999); Lesburg et al., Nat. Struct. Biol. 6: 937–943 (1999)]. This fully enclosed conformation is the result of the extensive interactions between the fingers and thumb subdomains which are likely to be unique to viral RdRps. In addition, a HCV-specific hairpin structure located in the thumb subdomain, which is absent in PV 3D$^{pol}$ and HIV RT, protrudes into the active site and may impose steric hindrance to accommodate double-stranded RNA molecules (Bressanelli, supra; Lesburg, supra). A highly conserved RNA binding groove bordered by the fingers subdomain and the interdomain loops provides the positively charged molecular surface to be occupied by the 5' overhang of the template (Bressanelli, supra; Lesburg, supra). Upon template/primer binding, NS5B is expected to undergo local conformational changes including those proposed for the β-hairpin and the thumb subdomain (Bressanelli, supra; Lesburg, supra). No large-scale domain movements, such as those observed in HIV RT [Huang et al., Science 286: 2305–2309 (1999)], are expected. At present, it is not clear how such conformational changes can be induced, in particular those required for accommodation of the nascent double-stranded RNA.

Based on the unliganded NS5B structure, the β-hairpin loop is located within a space similar to that of the N-terminal domain of T7 RNA polymerase [Bressanelli supra; Cheetham & Steitz, Science 286: 2305–2309 (1999)]. In the quaternary complex of T7 RNA polymerase, this N-terminal domain functions as a wedge to separate the nascent RNA strand from the DNA template (Cheetham & Steitz, supra). Whether or not the β-hairpin in NS5B serves a similar function will be the focus of future studies. At present, structure-guided mutations are being introduced to further investigate the functional role of the β-hairpin.

So far, two forms of in vitro RNA synthesis activities have been demonstrated for HCV NS5B. One is primer-dependent [Behrens et al., EMBO J. 15: 12–22 (1996); De Francesco et al., Methods Enzymol. 275: 58–67 (1996); Ferrari et al., J. Virol. 73: 1649–1654 (1999); Lohmann et al., J. Virol. 71: 8416–8428 (1997)]; the other is primer-independent or de novo initiated [(Luo et al., J. Virol. 74: 851–863 (2000); Oh et al., J. Virol. 73: 7694–7702 (1999); Zhong et al., J. Virol. 74: 2017–2022 (2000)]. It is generally believed that de novo initiation is the mode of HCV RNA replication in vivo since this mode insures the faithful replication of the entire viral genome by initiating RNA synthesis from the exact 3' terminus of the template RNA. However, it is not clear what mechanisms are involved in the initial priming steps of the replication process. Based on the findings reported in this Example, it is proposed that HCV NS5B binds viral RNA containing a 3' single-stranded overhang free of secondary structures. Following RNA binding, the initiating nucleotide (ATP for negative-strand synthesis and GTP for positive-strand synthesis) enters the active site through the conserved NTP channel and basepair with the 3' terminal template base of the viral RNA. It is believed that this step is sensitive to NTP concentration and is thus rate-limiting. Subsequently, the polymerase will add one or more nucleotides to the initiating nucleotide to produce short RNAs. These short RNA primers may dissociate from the polymerase complexes, a process that has been classified as abortive initiation/cycling [Carpousis and Gralla, Biochemistry 19: 3245–3253 (1980)]. These released short primers (predominantly di- or trinucleotides) can then be used as the primers by the enzyme to initiate new rounds of RNA synthesis in a fashion as described in this study. This may significantly accelerate the initiation process of RNA replication by circumventing the initial rate-limiting single nucleotide priming step. It is conceivable that base-pairing with di- or trinucleotide primers is more efficient than with a single NTP. Whether di- or trinucleotide-primed RNA synthesis indeed occurs in vivo can only be addressed in the context of a viral infection. Nonetheless, identification of the optimal template and primer pairs for HCV NS5B will facilitate the mechanistic characterization of nucleotide incorporation catalyzed by this enzyme and subsequent characterization of inhibitor compounds that target this enzyme.

Modifications and variations of this invention can be made without departing from its spirit and scope, as will be apparent to those skilled in the art. The specific embodiments described herein are offered by way of example only, and the invention is to be limited only by the appended claims, together with the full scope of equivalents to which such claims are entitled.

What is claimed is:

1. An assay system for detecting HCV replicase activity comprising an enzymatically active amount of HCV NS5B protein;

RNA template which comprises at least five nucleotides;

an RNA primer which is complementary to the 3' terminus of the template and comprises two or three nucleotides, wherein the template and primer do not form stable duplex solution in the absence of the NS5B protein, ATP, GTP, CTP, and UTP nucleotlde triphosphates (NTPs), wherein only one of the NTPs or the primer is radiolabeled; and an assay buffer that permits replication activity of the NS5B protein.

2. The assay system according to claim 1, wherein the base of the first nucleotide of the primer is a guanine.

3. The assay system according to claim 1, wherein the NS5B protein is in contact with an inhibitory compound of the NS5B protein.

4. The assay system according to claim 1, wherein the NS5B protein is a soluble enzymatically active NSB5B protein expressed in *Escherichia coli*.

5. The assay system according to claim 1, wherein the RNA template lacks any stable secondary structure at the 3' terminus.

6. The assay system according to claim 1, wherein the radiolabeled NTP or primer comprises a phosphate isotope.

7. The assay system according to claim 6, wherein the radiolabeled NTP is an α-$^{33}$P-NTP which hydrogen bonds to a nucleotide of the template.

8. The assay system according to claim 1, wherein the assay buffer comprises 50 mM HEPES (pH 7.3), 10 mM β-mercaptoethanol, 50 mM NaCl, and 5 mM MgCl$_2$;

the template RNA is 5 μM;

the primer is 10 μM;

the HCV NS5B protein is 3 to 5 μM; and the NTP substrate is 100 μM.

9. A method for detecting HCV replicase activity, comprising (a) providing an assay system comprising an enzymatically active amount of HCV NS5B protein;

an RNA template which comprises at least five nucleotides;

an RNA primer which is complementary to the 3' terminus of the template and comprises two or three nucleotides, wherein the template and primer do not form stable duplex in solution in the absence of the NS5B protein, ATP, GTP, CTP, and UTP nucleotide triphosphates (NTPs), wherein one of the NTPs or the primer is radiolabeled; and an assay buffer that permits replication activity of the NS5B protein;

(b) incubating said assay system under conditions that permit NS5B polymerase activity; and detecting a nucleic acid synthesized by the HCV NS5B protein.

10. The method according to claim 9, wherein said detecting comprises evaluating an autoradiograph of reaction products separated by gel electrophoresis.

11. The method according to claim 9, wherein the NS5B protein is a soluble NS5B protein expressed in *Escherichia coli*.

12. The method according to claim 9, wherein the base of the first nucleotide of the primer is a guanine.

13. The method according to claim 9, wherein the radiolabeled NTP or primer comprises a phosphate isotope.

14. The method according to claim 13, wherein the radiolabeled NTP is an α-$^{33}$P-NTP which hydrogen bonds to a nucleotide of the template.

15. The method according to claim 9, wherein the assay buffer comprises 50 mM HEPES (pH 7.3), 10 mM β-mecaptoethanol, 50 mM NaCl, and 5 mM MgCl$_2$;

the template RNA is 5 μM;

the primer is 10 μM;

the HCV NS5B protein is 3–5 μM;

the NTP is 100 μM; and the assay is performed at 30° C.

16. The method according to claim 9, wherein said assay system further comprises a candidate inhibitory compound.

17. The method according to claim 16, wherein said method is a high throughput screen.

18. The method according to claim 16, wherein said candidate inhibitory compound directly interferes with the replicase activity of the NS5B protein.

19. The assay system according to claim 1, wherein said HCV NS5B protein, RNA template and RNA primer form a replicase complex.

* * * * *